United States Patent [19]

Porter et al.

[11] Patent Number: 4,590,927

[45] Date of Patent: May 27, 1986

[54] UNITARY, INFLATABLE PENILE PROSTHESIS SYSTEM

[75] Inventors: Christopher H. Porter, Minnetonka; Charles C. Kuyava, Brooklyn Center, both of Minn.

[73] Assignee: American Medical Systems, Inc., Minnetonka, Minn.

[21] Appl. No.: 705,508

[22] Filed: Feb. 25, 1985

[51] Int. Cl.[4] ............................................. A61F 5/00
[52] U.S. Cl. .................................................. 128/79
[58] Field of Search .................. 128/79, DIG. 25; 3/1

[56] References Cited

U.S. PATENT DOCUMENTS

| | | | |
|---|---|---|---|
| 4,267,829 | 5/1981 | Burton et al. | 128/79 |
| 4,318,396 | 3/1982 | Finney | 3/1 |
| 4,353,360 | 10/1982 | Finney | 128/79 |
| 4,369,771 | 1/1983 | Trick | 128/79 |
| 4,383,525 | 5/1983 | Scott et al. | 3/1 |
| 4,407,278 | 10/1983 | Burton | 128/79 |

Primary Examiner—Robert Peshock
Assistant Examiner—Cary E. Stone
Attorney, Agent, or Firm—Arnold, White & Durkee

[57] ABSTRACT

A unitary, inflatable penile prosthesis system includes a prosthesis implantable within the corpus cavernosum of the penis in order to alleviate erectile impotency. A tubular enclosure includes a distal pump, a medial pressurizable chamber, and a proximal fluid reservoir. A pump draws fluid from the reservoir through an external fluid passageway into the pressurizable chamber. The pressurizable chamber is defined by an internal, tubular, substantially nondistensible portion and a concentric tubular sleeve. The nondistensible portion is crimped so that it may expand in diameter. Upon expansion, the prosthesis assumes a straight, erect state. The sleeve may elastically bias the nondistensible portion to its flaccid state. Fluid for filling the nondistensible portion may be stored in a rear fluid reservoir having a rigid internal stabilizer.

33 Claims, 6 Drawing Figures

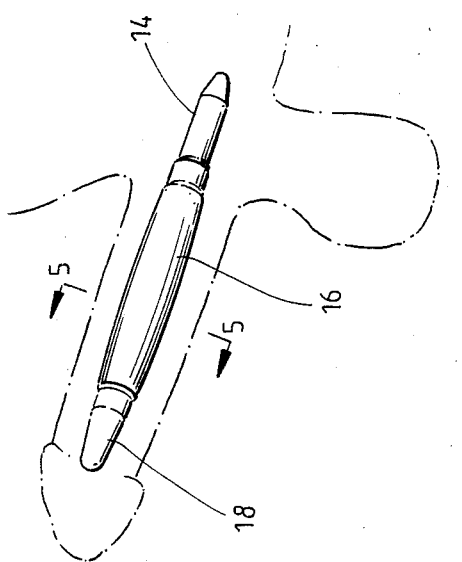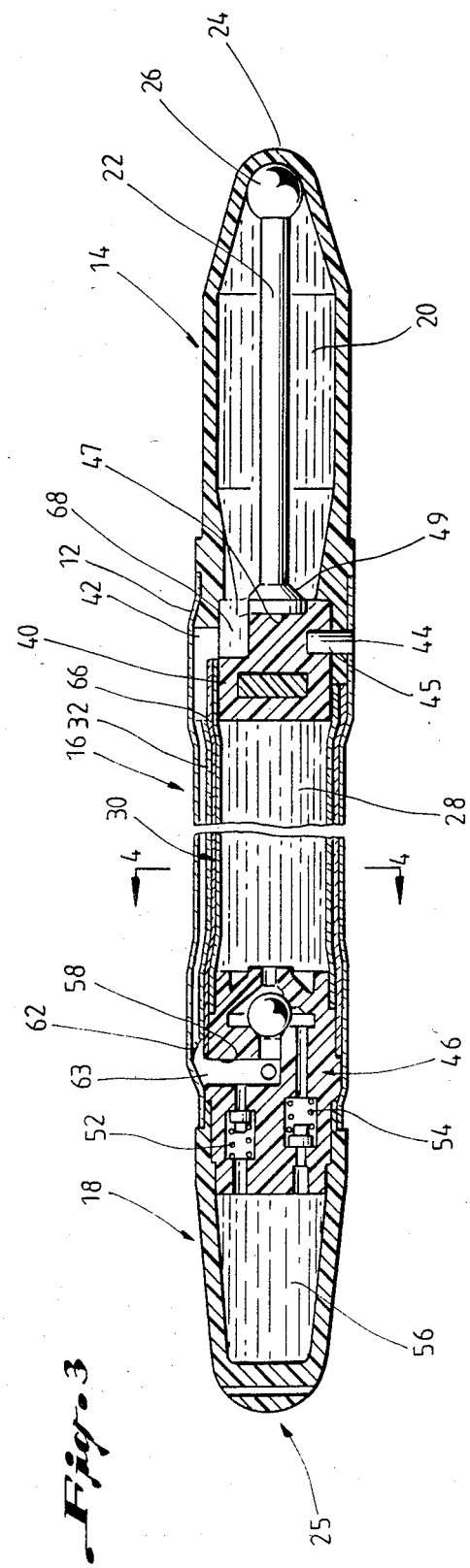

UNITARY, INFLATABLE PENILE PROSTHESIS SYSTEM

BACKGROUND OF THE INVENTION

1. Field of the Invention

This invention relates generally to methods and devices for alleviating erectile impotency, and specifically to unitary, inflatable devices which may be implanted within the corpus cavernosum of the penis.

2. Brief Description of the Background Art

A number of devices are commercially available for enabling those with erectile impotency to achieve an erection. These devices are generally implanted within the corpus cavernosum of the penis. Normally two such devices are utilized, one implanted into each corpus cavernosum. Modern day technology has evolved from the early rigid rod devices that produced a permanent erection. Since the user had no ability to control the operation of the device, the rigid rod approach had serious drawbacks.

The so-called inflatable penile prostheses generally include a reservoir, a pump, and a pressure chamber. Fluid is pumped from the reservoir by the pump to the pressure chamber in order to achieve an erection. Early devices such as that disclosed in U.S. Pat. No. 3,853,122 to Strauch, et al., used an external pump and a simple tube and valve mechanism. U.S. Pat. No. 3,954,102 to Buuck discloses an improvement wherein the device may be manually operated in a convenient fashion through the use of a bypass valve means.

U.S. Pat. No. 4,009,711 discloses a penile prosthesis with an external pump and a non-distensible tail that is implanted at the root of each corpus cavernosum under the puboischiatic rami. The patent indicates that the taillike portion provides increased stability when the penis becomes erect and decreases considerably the volume of fluid needed for an adequate erection.

A penile prosthesis using an inflatable hinge is described in U.S. Pat. No. 4,267,829 to Burton and Mikulich. In this patent, a tubular section includes a chamber which undergoes only a small change in volume and therefore requires minimum fluid displacement as the prosthesis transforms from a non-erect to an erect condition. Unitary penile prostheses which include a pair of concentric chambers, one of which is pressurized, are disclosed in U.S. Pat. Nos. 4,353,360 and 4,399,811. In these patents, the inner of two concentric chambers is pressurized while the outer of the two chambers acts as the fluid reservoir prior to erection. To attain an erection, fluid is pumped from the outer reservoir through a pump to the inner reservoir. Thus, the total volume of the two chambers is always constant.

SUMMARY OF THE INVENTION

The present invention provides a dependable, unitary, inflatable penile prosthesis with a low fluid volume that is convertable from a non-erect to an erect state without requiring a substantial volume change. The volume of the portion of the device that includes the pressurizable chamber increases when transformed to the erect state. The medial portion of the prosthesis may be smaller in the flaccid state and may deflate readily and naturally. Moreover, a fluid reservoir external of the pressurizable chamber is provided that may add a fluid volume safety factor.

In accordance with one preferred embodiment of the present invention, a unitary penile prosthesis implantable within at least one corpus cavernosum of the penis includes an implantable, broadly tubular enclosure. A generally tubular pressurizable chamber section is defined medially within the enclosure. The chamber section includes a substantially nondistensible tubular portion and a tubular sleeve concentric with the tubular portion. The tubular portion is expandable from a flaccid to an erect state when the interior volume of the tubular portion is substantially filled to capacity. A fluid containing reservoir is defined within the enclosure in series along the length of the enclosure with respect to the chamber section. A manually compressible pump is defined within the enclosure in series along the length of the enclousre with respect to the chamber section. The pump is adapted for fluid communication with the tubular portion. A passageway fluidically connects the reservoir and the pump while being maintained in fluid isolation from the chamber section. The pump is adapted to pump fluid to the tubular portion from the reservoir such that the volume of the chamber section increases as the chamber section is transformed from its flaccid to its erect state.

In accordance with another preferred embodiment of the present invention, a unitary penile prosthesis implantable within the corpus cavernosum of the penis includes an implantable, broadly tubular enclosure. A generally tubular pressurizable chamber section is defined medially within the enclosure. The chamber section includes a substantially nondistensible tubular portion and a tubular sleeve concentric with the tubular portion. The tubular portion is expandable from a flaccid to an erect state when the interior volume of the tubular portion is filled substantially to capacity. A fluid containing reservoir is defined within the enclosure in series along the length of the enclosure with respect to the chamber section. The reservoir is capable of holding a substantial portion of the fluid needed to transform the tubular portion from its flaccid to its erect state. A manually compressible pump is defined within the enclosure in series along the length of the enclosure with respect to the chamber section. The reservoir and the pump may be located on opposite ends of the chamber section. The pump is adapted for fluid communication with the chamber section. The passageway fluidically connects the reservoir and the pump so that the passageway is maintained in fluid isolation from the chamber section.

In accordance with yet another preferred embodiment of the present invention, a unitary inflatable penile prosthesis implantable within at least one corpus cavernosum includes an implantable, broadly tubular enclosure. A generally tubular pressurizable chamber section is defined medially within the enclosure. The chamber section includes a substantially nondistensible tubular portion and a tubular sleeve concentric with and surrounding the tubular portion. The tubular portion is expandable from a flaccid to an erect state when the interior volume of the tubular portion is filled substantially to capacity. A fluid containing reservoir is defined within the enclosure in series along the length of the enclosure. The reservoir is adapted to be proximally situated with respect to the chamber section and includes a rigid internal stabilizing member. The reservoir is capable of holding a substantial portion of the fluid needed to transform the tubular portion from its flaccid to its erect state, such that the volume within the sleeve in the erect state is greater than the volume within the sleeve in the flaccid state. A manually compressible pump is defined within the enclosure in a series along the length of the enclosure with respect to the chamber section. The pump is adapted for fluid communication with the chamber section. A passageway fluidically connects the reservoir and the pump in fluid isolation from the chamber section.

In accordance with another preferred embodiment of the present invention, a unitary inflatable penile prosthesis implantable within at least one corpus cavernosum of the penis includes an implantable, broadly tubular enclosure having a front tip that is substantially rigid in the erect state. A tubular pressurizable chamber section is defined medially within the enclosure. The chamber section includes a substantially nondistensible tubular portion and a tubular sleeve concentric with the tubular portion. The tubular portion is expandable from a flaccid to an erect state when the interior volume of the tubular portion is filled substantially to capacity. A fluid containing reservoir is defined within the enclosure in series along the length of the enclosure with respect to the chamber section. The reservoir is adapted to hold a substantial portion of the fluid needed to transform the tubular portion from its flaccid to its erect state such that the volume of the chamber section increases as the chamber section is transformed from its flaccid to its erect state. A manually compressible pump is defined within the enclosure in a series along the length of the enclosure with respect to the chamber section. The pump is adapted for fluid communication with the chamber section. A passageway fluidically connects the reservoir and the pump. The passageway is maintained in fluid isolation from the chamber section.

In accordance with still another preferred embodiment of the present invention, a method for simulating an erection includes the step of providing an implantable, broadly tubular enclosure and a generally tubular pressurizable chamber section defined medially within the enclosure. The chamber section includes a substantially nondistensible tubular portion defining an inner volume surrounded by a tubular sleeve defining a composite volume including the inner volume. The chamber section is transformed from a flaccid to an erect state by pressurizing the inner volume with fluid transferred at least in part from within the enclosure but outside the tubular sleeve. The amount of fluid within the composite volume is increased until the nondistensible tubular portion becomes rigid and pressurized.

BRIEF DESCRIPTION OF THE DRAWINGS

FIG. 1 is a side elevational view of one embodiment of the present invention, in use, in its flaccid state;

FIG. 2 is a side elevation view of the embodiment shown in FIG. 1 in its erect state;

FIG. 3 is an enlarged vertical cross-sectional view taken generally along the curve 3—3 in FIG. 1;

DESCRIPTION OF A PREFERRED EMBODIMENT

Figure 4:
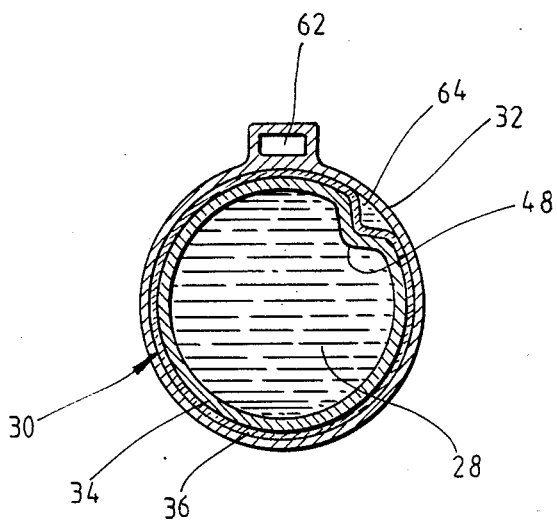
FIG. 4 is a cross-sectional view taken generally along the line 4—4 in FIG. 1 of one embodiment in the flaccid state.

Referring to the drawing wherein like reference characters are utilized for like parts throughout the several views, a unitary, inflatable penile prosthesis 10, shown in FIG. 1, includes an implantable, broadly tubular enclosure 12 sized to be implanted within one corpus cavernosum of the penis. Normally two devices of the kind shown in FIG. 1 are implanted, one in each corpus cavernosum. However, the present invention is adaptable for use with double cylinder designs in which one prosthesis is used to fill both corpus cavernosa. The outer layer of the tubular enclosure 12 is advantageously made up of material which is biocompatible. One particularly suitable material for this purpose is silicone, since it is readily accepted by the human body when used with indwelling devices.

The enclosure 12 includes a proximal section 14, a pressurizable medial section 16, and a distal portion 18. Normally the proximal section 14 is positioned in the rear of the corpus cavernosum under the puboischiatic rami. As shown in FIG. 3, the proximal section 14 defines a rear fluid reservoir 20. A rigid stabilizer 22 extends rearwardly from the medial section 16 centrally through the fluid reservoir 20 to a rounded end 26 in contact with the rear tip 24. The stabilizer 22 serves to maintain the shape of the rear fluid reservoir 20 and provide rigidity regardless of the amount of fluid contained therein. Conveniently the rear tip 24 has a slightly tapered external configuration as a result. A conventional rear tip extender (not shown) may be provided to lengthen the enclosure 12, if necessary.

The distal section 18 advantageously includes a front tip 25 that is substantially rigid, so as to resist buckling during intercourse, at least in the erect state. Advantageously the tip 25 is rigid in both the erect and flaccid states. If desired, the front tip may be made substantially solid.

The medial section 16 defines a pressurizable chamber 28. The medial section 16 is positioned along the length of the enclosure 12 such that it tends to lie medially along the length of the corpus cavernosum and particularly so that it lies substantially in the portion of the corpus cavernosum which is distal of the body plane. Thus, the pressurizable chamber 28 may provide an inflatable hinge, as will be described in greater detail hereinafter.

As shown in FIG. 4, the pressurizable chamber 28 is defined by a tubular portion 30 which is concentrically contained within a tubular sleeve 32. The tubular portion 30 may be formed of two layers including an inner layer or bladder 34 and a substantially non-distensible layer 36. The non-distensible layer 36 may take a variety of forms, but advantageously it is formed from a tubular section of woven dacron material, such as a prosthetic vascular graft. The inner layer 34 may be formed of a substantially liquid impervious material, such as silicone.

Adjacent proximal ends of the tubular portion 30 and tubular sleeve 32 are anchored to the plug 40 which also secures the distal end of the stabilizer 22, as shown in FIG. 3. The plug 40 fills the internal volume of the enclosure 12 with the exception of an axial passageway 42.

On the distal end of the pressurizable chamber 28, the tubular portion 30 and sleeve 32 are anchored to the valve plug 46. Like the plug 40, the valve plug 46 fills a portion of the interior of the enclosure 12. In this way, the intermediate portion of the tubular sleeve 32 and portion 30 extend between the plugs 40 and 46 in an unsupported fashion. Thus, when the prosthesis 10 is in a flaccid state, as shown in FIG. 1, the portion 30 and sleeve 32 may tend to neck or sag inwardly.

Figure 5:
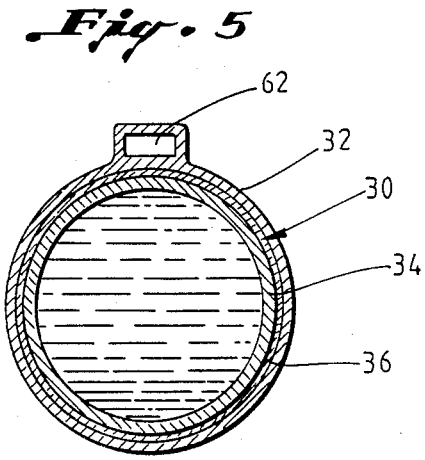
FIG. 5 is a cross-sectional view taken generally along the line 5—5 in FIG. 2 of one embodiment in the erect state.

As shown in FIG. 4, the tubular portion 30, in its flaccid state, includes a crimp or fold 48. The crimp 48 provides for extra expansion of the tubular portion 30 in order to completely fill the tubular sleeve 32 in its expanded configuration. Because of the nature of the material of the portion 30, it generally expands in girth to a full tubular configuration, as shown in FIG. 5, and then comes to a complete stop after which no further expansion or distension is possible. Thus the change in volume between the position shown in FIG. 4 and the position shown in FIG. 5 wherein the portion 30 is essentially unfolded, is relatively small.

The tubular sleeve 32 may be distensible or non-distensible. In one preferred embodiment it is made of a distensible, stretchable, elastic material such as silicone. With an elastic sleeve 32 the relaxed volume of the sleeve 32 may correspond closely to the flaccid volume of the portion 30 so that the sleeve 32 always conforms closely to the configuration of the portion 30. Moreover, with an elastic sleeve 32, the sleeve 32 elastically resists the expansion of the tubular portion 30 from its flaccid to its erect state.

Figure 6:
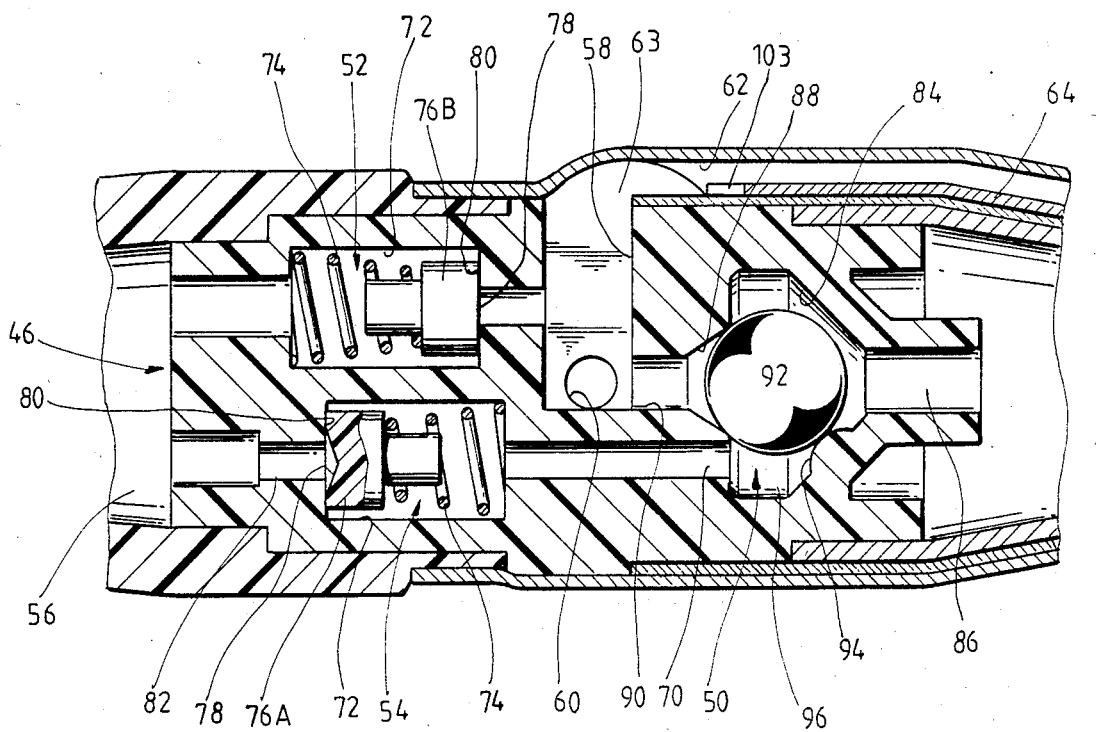
FIG. 6 is an enlarged cross-sectional view of the valving portion of the prosthesis shown in FIG. 3.

The valve plug 46, shown in FIG. 6, includes a bypass valve 50, an inlet valve 52, and an exit valve 54. The inlet valve 52 communicates on one end with a manually compressible pump 56 defined within the distal portion 18 of the enclosure 12. The inlet valve 52 communicates on its proximal end with a radially oriented passageway 58. The radially oriented passageway 58 communicates with a transverse, radially oriented passageway section 60. The passageway 58 and the section 60 communicate with an axial, lengthwise passageway 62 by way of the annular chamber 63 defined by the sleeve 32. The passageway 62 extends from the distal portion 18 to the proximal portion 14 in fluid isolation from the pressurizable chamber 28. It empties into the axial passageway 42 and ultimately into the rear fluid reservoir 20.

Regardless of the state of the portion 30 and sleeve 32, communication through the passageway 62 is always possible. The passageway 62 also communicates with the region 64 between the portion 30 and sleeve 32, but only at the point 66 adjacent the axial passageway 42 and at the point 103 adjacent the axial passageway 63. Thus the fluid within the region 64 may be exhausted rearwardly through the prosthesis 10 into the slot 68 defined in the plug 40 and stabilizer 22.

The outlet valve 54, shown in FIG. 6, communicates with the manually compressible pump 56 on the distal end and communicates on the other end with the region surrounding the bypass valve 50. Specifically a continuously open passageway 70 is provided across the bypass valve 50 to the interior of the tubular portion 30.

Each of the valves 52 and 54 includes an enlarged housing 72, a coiled spring 74 and a valve member 76. The coiled spring 74 biases the valve member 76A of the valve 54 distally while the coiled spring 74 of the valve 52 biases its valve member 76B proximally. The sealing face 78 of each valve 52, 54 seals on an adjacent transversely oriented ledge 80. The sealing faces 78 of the valves 52 and 54 are concave which encourages formation of a good seal. The valves 52, 54 each include a necked down region 82 in the housing 72 proximate to the ledge 80.

The bypass valve 50 includes a generally conical housing 84 with a proximally extending port 86 and a distally extending seat 88. The seat 88 is generally conical as well and communicates with the passageway 90 that in turn communicates with the passageway 58. A ball 92 is normally seated on the seat 88 closing the passageway 90. One or more extensions 94 defined on the conical housing 84 aligned with the passageway 96 permit generally continuous fluid communication from the passageway 96 to the interior of the tubular portion 30. However, reverse flow into the passageway 90 is normally prevented by the ball 92.

A filling port 44 may enable fluid communication between the exterior of the enclosure 12 and the rear fluid reservoir 20 for fluid insertion. A hypodermic needle may be inserted into the port 44 through a central aperture 47 in the base 49 of the stabilizer 22. When the end of the needle reaches the slot 68, the fluid then flows into the reservoir 20. After the needle is retracted the port 44 is filled with a sealant 45.

The prosthesis 10 may be operated in the following fashion. Initially a sufficient amount of fluid, such as a physiological solution, is loaded into the rear fluid reservoir 20 and tubular portion 30. The fluid may be inletted to the fluid reservoir 20 initially and then pumped to the portion 30 as will be described hereinafter. In any case, the portion 30 contains sufficient fluid to assume the configuration shown in FIG. 4. In the flaccid state the portion may contain at least about 50% of its capacity and in one illustrative embodiment it contains about 90% of its capacity.

The rear fluid reservoir 20 is filled with at least a substantial portion of fluid needed to permit pumping of the fluid from the reservoir 20 through the pump 56 to fill the added tubular portion 30 volume required to transform from the flaccid state shown in FIGS. 1 and 4 to the erect, filled to capacity state shown in FIGS. 2 and 5 wherein the tubular portion 30 is taut and pressurized. For example, the reservoir 20 may contain from about 20% and 100% of the fluid needed to transform the portion 30 to its erect state. Advantageously, the reservoir 20 contains from about 50% to about 70% of the fluid needed to transform the chamber 28 from the flaccid to the erect state. Additional fluid volume to pressurize the tubular portion 30 may be stored, for example, in the space 64 between the sleeve 32 and portion 30. Normally it will be necessary for the rear reservoir 20 and other fluid storage volumes to contain slightly more fluid than that which would be held in the difference in the tubular portion 30 volumes shown in FIGS. 4 and 5, because it is necessary to prime the various pumping passageways in order to get sufficient fluid to the tubular portion 30. Also, it is desirable to provide additional fluid capacity as a safety factor to insure that an erection can be maintained under all normal circumstances. In any case, the necessary fluid amounts can be easily determined in practice by those skilled in the art, and depend on the sizes of the various components utilized.

The prothesis 10 is then implanted within the corpus cavernosum of the patient. This may be done using conventional surgical techniques well known in the implantation of inflatable penile prostheses. The proximal section 14 is positioned in the rear region of the corpus cavernosum and the distal section 18 in the distal region of the corpus cavernosum. It may be necessary in certain circumstances to use rear tip extenders for the proximal end in a fashion well known in the art to achieve a correct fit.

In order to operate the implanted prosthesis 20, the user initially compresses the manually compressible pump 56 externally of the penis. The compression of the flexible manually compressible pump 56 forces any fluid contained within the pump 56 into the pressurizable chamber 28. This is because the pressure increase within the pump 56 forces the valve 54 open allowing fluid to flow around the valve member 76A through the passageway 70 past the ball 92 and around an extension 94. The user may continue to successively depress the pump 56 until the pressure within the pressurizable chamber 28 becomes sufficiently great that the valve member 76A no longer unseats from the sealing surface 78. At the same time, the compression of the pump 56 seals the inlet valve 52 closed.

Each time the user releases the pump 56, its walls spring back to their original position. This creates suction within the pump 56, opening the valve 52 and drawing fluid into the pump 56. The fluid is drawn from the reservoir 20 through the passageway 62. When the suction subsides, the valve 52 springs closed.

In the erect or substantially rigid configuration, the tubular portion 30 and sleeve 32 are puffed outwardly slightly from the configuration shown in FIGS. 1, 3, and 4, to that illustrated in FIGS. 2 and 5. Moreover, the prosthesis 10 is straight rather than angled or L-shaped. The sleeve 32 is stretched radially outwardly so as to fit snugly about the tubular portion 30.

In the flaccid state, the prosthesis 10 bends to accommodate to the natural flaccid shape of the penis. The bending occurs along the pressurizable chamber 28 which essentially acts as a hinge.

To resume the flaccid state after an erection, the valve plug 46 is squeezed externally. As a result of the deformation of the conical housing 84 and seat 88, fluid is allowed to flow from the pressurizable chamber 28 past the ball 92 and into the passageway 90. From there the fluid may flow through the passage 60 or the passage 58 to the passageway 62. Because of the pent up pressure within the pressurizable chamber 28, the fluid is forced rearwardly through the passageway 62 into the rear fluid reservoir 20 where it is stored for use in the next erection. When the pressure within the chamber 28 has subsided sufficiently, manual actuation of the bypass valve 50 no longer has any effect on fluid outflow from the pressurizable chamber 28 and the prosthesis 10 is in equilibrium. In this state the prosthesis 10 assumes a substantially flaccid configuration and bends with the penis so as to fold along the pressurizable chamber 28.

With the present invention the volume of the pressurizable chamber 28 is nonconstant during expansion to erection. This is because at least a portion of the fluid required to achieve the erect state is obtained from sources external of the chamber 28, for example from the rear reservoir 20. Thus, the volume of the chamber 28 increases as the chamber 28 transforms to its erect state.

A fluid volume safety factor may be provided, with the present invention, without increasing the necessary girth of the flaccid prosthesis. This is because additional available volume may be provided without enlarging the medial portion 16 of the flaccid prosthesis.

With the present invention, the pressurizable chamber 28 and thus the prosthesis as a whole may be smaller in the flaccid state. The use of the rear reservoir 20 causes the device to take on a smaller flaccid configuration and to bend easily along the medial portion 16. In addition, the prosthesis may deflate more readily and naturally. This is because the tubular sleeve 32 forces the portion 30 to assume its deflated configuration by pressing the fluid outwardly of the pressurizable chamber 28.

Because the integrity of the fluid passageway 62 remains inviolate and uncrimped, the egress of fluid from the pressurizable chamber 28 is assured and may be carried on in a relatively smooth fashion. Also, because the distension of the portion 30 is minimized, the tendency for faults or creases to block operation of the prosthesis 10 is lessened.

While the present invention has been described with respect to a single preferred embodiment, those skilled in the art will appreciate a number of variations and modifications therefrom, and it is intended to cover within the appended claims all modifications and variations that fall within the true spirit and scope of the present invention.

What is claimed is:

1. A unitary inflatable penile prosthesis implantable within at least one corpus cavernosum of the penis, said prosthesis comprising:
    an implantable, broadly tubular enclosure;
    a generally tubular pressurizable chamber section defined medially within said enclosure, said chamber section including a substantially nondistensible tubular portion and tubular sleeve concentric with said tubular portion, said tubular portion being expandable from a flaccid to an erect state when the interior volume of said tubular portion is filled substantially to capacity;
    a fluid containing reservoir defined within said enclosure in series along the length of said enclosure with respect to said chamber section;
    a manually compressible pump defined within said enclosure in series along the length of said enclosure with respect to said chamber section, said pump adapted for fluid communication with said tubular portion, said reservoir and said pump being located on opposite sides of said chamber section; and
    a passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state.

2. The prosthesis of claim 1 wherein said pump is located distally of said chamber section.

3. The prosthesis of claim 1 wherein said passageway is defined as a narrow channel extending axially along the length of said prosthesis externally of said tubular pressurizable chamber section.

4. The prosthesis of claim 1 wherein said tubular portion is crimped in its flaccid state.

5. The prosthesis of claim 4 wherein said crimp extends radially inwardly and is arranged lengthwise with respect to the prosthesis.

6. The prosthesis of claim 4 wherein the region between said tubular portion and said sleeve communicates with said reservoir.

7. The prosthesis of claim 1 wherein said sleeve surrounds said tubular portion.

8. The prosthesis of claim 7, wherein said tubular portion includes an outer layer of non-distensible material and an inner flexible layer.

9. The prosthesis of claim 1 wherein said tubular sleeve resiliently biases said tubular portion towards its flaccid configuration.

10. The prosthesis of claim 9 wherein said sleeve is maintained in contact with said tubular portion in both the erect and flaccid states.

11. The prosthesis of claim 1 wherein said reservoir is adapted to contain enough fluid to fill the volume of said sleeve.

12. The prosthesis of claim 1 including a manually operable release valve operable from outside said enclosure to allow fluid flow from said chamber section to said reservoir.

13. The prosthesis of claim 1 including a relatively rigid stabilizer maintained within the interior of said reservoir.

14. The prosthesis of claim 1 wherein said sleeve surrounds and substantially conforms to said tubular portion in both the flaccid and erect states of said chamber section.

15. A unitary inflatable penile prosthesis implantable within at least one corpus cavernosum of the penis, said prosthesis comprising:
   an implantable, broadly tubular enclosure;
   a generally tubular pressurizable chamber section defined medially within said enclosure, said chamber section including a substantially nondistensible tubular portion and a tubular sleeve concentric with said tubular portion, said tubular portion being expandable from a flaccid to an erect state when the interior volume of said tubular portion is filled substantially to capacity;
   a fluid containing reservoir defined within said enclosure in series along the length of said enclosure with respect to said chamber section, said reservoir being capable of holding a substantial portion of the fluid needed to transform said tubular portion from its flaccid to its erect state;
   a manually compressible pump defined within said enclosure in series along the length of said enclosure with respect to said chamber section, said pump adapted for fluid communication with said tubular portion, said reservoir and said pump being located on opposite sides of said chamber section; and
   a passageway fluidically connecting said reservoir and said pump, said passageway being maintained in fluid isolation from said chamber section.

16. A unitary inflatable penile prosthesis implantable within at least one corpus cavernosum of the penis, said prosthesis comprising:
   an implantable, broadly tubular enclosure having a front tip that is substantially rigid in the erect state;
   a generally tubular pressurizable chamber section defined medially within said enclosure, said chamber section including a substantially nondistensible tubular portion and a tubular sleeve concentric with said tubular portion, said tubular portion being expandable from a flaccid to an erect state when the interior volume of said tubular portion is filled substantially to capacity;
   a fluid containing reservoir defined within said enclosure in series along the length of said enclosure with respect to said chamber section, said reservoir being adapted to hold a substantial portion of the fluid needed to transform said tubular portion from its flaccid to its erect state, such that the volume of said chamber section increases as said chamber section is transformed from its flaccid to its erect state;
   a manually compressible pump defined within said enclosure in series along the length of said enclosure with respect to said chamber section, said pump adapted for fluid communication with said chamber, said pump and said reservoir being located on opposite sides of said chamber section; and
   a passageway fluidically connecting said reservoir and said pump, said passageway being maintained in fluid isolation from said chamber section.

17. The prosthesis of claim 16 wherein said front tip is substantially rigid in both said flaccid and erect states.

18. The prosthesis of claim 16 wherein said pump is adapted to be oriented distally of said chamber section and said front tip extends distally of said pump.

19. A method for simulating an erection comprising the steps of:
   providing an implantable, broadly tubular enclosure and a generally tubular pressurizable chamber section defined medially within the enclosure, said chamber section including a substantially nondistensible tubular portion surrounded by a tubular sleeve, said tubular portion defining an inner volume within said chamber section and said sleeve defining a composite volume, including said inner volume, within said sleeve;
   transforming said chamber section from a flaccid to an erect state by pressurizing said inner volume with fluid transferred at least in part from within said enclosure but outside said tubular sleeve;
   increasing the amount of fluid within said composite volume until said nondistensible tubular portion becomes rigid and pressurized; and
   maintaining said sleeve in contact with said tubular portion in both the erect and flaccid states.

20. The method of claim 19 wherein said transforming step includes the step of manually pumping fluid from outside said tubular sleeve into said tubular portion.

21. A unitary inflatable penile prosthesis implantable within at least one corpus cavernosum of the penis, said prosthesis comprising:
   an implantable, broadly tubular enclosure;
   a generally tubular pressurizable chamber section defined medially within said enclosure, said chamber section including a substantially nondistensible tubular portion and a tubular sleeve concentric with and surrounding said tubular portion, said tubular portion being expandable from a flaccid to an erect state when the interior volume of said tubular portion is filled substantially to capacity, said tubular portion being crimped in its flaccid state, the region between said tubular portion and said sleeve communicating with a fluid containing reservoir;
   said fluid containing reservoir defined within said enclosure in series along the length of said enclosure with respect to said chamber section,
   a manually compressible pump defined within said enclosure in series along the length of said enclosure with respect to said chamber section, said pump adapted for fluid communication with said tubular portion; and a passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state.

22. The prosthesis of claim 21 wherein said crimp extends radially inwardly and is arranged lengthwise with respect to the prosthesis.

23. A unitary inflatable penile prosthesis implantable within at least one corpus cavernosum of the penis, said prosthesis comprising:

an implantable, broadly tubular enclosure;
a generally tubular pressurizable chamber section defined medially within said enclosure, said chamber section including a substantially nondistensible tubular portion and a tubular sleeve concentric with said tubular portion, said tubular portion being expandable from a flaccid to an erect state when the interior volume of said tubular portion is filled substantially to capacity, said tubular sleeve resiliently biasing said tubular portion towards its flaccid configuration, such that said sleeve is maintained in contact with said tubular portion in both the erect and flaccid states;
a fluid containing reservoir defined within said enclosure in series along the length of said enclosure with respect to said chamber section;
a manually compressible pump defined within said enclosure in series along the length of said enclosure with respect to said chamber section, said pump adapted for fluid communication with said tubular portion; and
a passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state.

24. A unitary inflatable penile prosthesis implantable within at least one corpus cavernosum of the penis, said prosthesis comprising:

an implantable, broadly tubular enclosure;
a generally tubular pressurizable chamber section defined medially within said enclosure, said chamber section including substantially nondistensible tubular portion and a tubular sleeve concentric with said tubular portion, said tubular portion being expandable from a flaccid to an erect state when the interior volume of said tubular portion is filled substantially to capacity, said sleeve surrounding and substantially conforming to said tubular portion in both the flaccid and erect states of said chamber section;
a fluid containing reservoir defined within said enclosure in series along the length of said enclosure with respect to said chamber section;
a manually compressible pump defined within said enclosure in series along the length of said enclosure with respect to said chamber section, said pump adapted for fluid communication with said tubular portion; and
a passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state.

25. The prosthesis of claim 24 wherein said tubular sleeve resiliently biases said tubular portion towards its flaccid configuration.

26. A unitary inflatable penile prosthesis implantable within at least one corpus cavernosum of the penis, said prosthesis comprising:

an implantable, broadly tubular enclosure;
a generally tubular pressurizable chamber section defined medially within said enclosure, said chamber section including a substantially nondistensible tubular portion and a tubular sleeve concentric with said tubular portion, said tubular portion being expandable from a flaccid to an erect state when the interior volume of said tubular portion is filled substantially to capacity, said sleeve surrounding and substantially conforming to said tubular portion in both the flaccid and erect states of said chamber section;
a fluid containing reservoir defined within said enclosure in series along the length of said enclosure with respect to said chamber section, said reservoir being capable of holding a substantial portion of the fluid needed to transform said tubular portion from its flaccid to its erect state;
a manually compressible pump defined within said enclosure in series along the length of said enclosure with respect to said chamber section, said pump adapted for fluid communication with said tubular portion; and
a passageway fluidically connecting said reservoir and said pump, said passageway being maintained in fluid isolation from said chamber section.

27. The prosthesis of claim 26 wherein said tubular sleeve resiliently biases said tubular portion toward its flaccid configuration.

28. A unitary inflatable penile prosthesis implantable within at least one corpus cavernosum of the penis, said prosthesis comprising:

an implantable, broadly tubular enclosure having a front tip that is substantially rigid in the erect state;
a generally tubular pressurizable chamber section defined medially within said enclosure, said chamber section including a substantially nondistensible tubular portion and a tubular sleeve concentric with said tubular portion, said tubular portion being expandable from a flaccid to an erect state when the interior volume of said tubular portion is filled substantially to capacity, said sleeve surrounding and substantially conforming to said tubular portion in both the flaccid and erect states of said chamber section;
a fluid containing reservoir defined within said enclosure in series along the length of said enclosure with respect to said chamber section, said reservoir being adapted to hold a substantial portion of the fluid need to transform said tubular portion from its flaccid to its erect state, such that the volume of said chamber section increases as said chamber section is transformed from its flaccid to its erect state;
a manually compressible pump defined within said enclosure in series along the length of said enclosure with respect to said chamber section, said pump adapted for fluid communication with said chamber section; and a passageway fluidically connecting said reservoir and said pump, said passageway being maintained in fluid isolation from said chamber section.

29. The prosthesis of claim 28 wherein said tubular sleeve resiliently biases said tubular portion towards its flaccid configuration.

30. A unitary inflatable penile prosthesis implantable within at least one corpus cavernosum of the penis, said prosthesis comprising:
  a generally tubular pressurizable chamber section defined along said prosthesis, said chamber section including a tubular portion and a distensible tubular sleeve concentric with said tubular portion, said tubular portion being transformable from flaccid to an erect state, said distensible tubular sleeve having a volume in the flaccid state that is less than the capacity of said tubular portion; and
  a fluid containing reservoir and a manually compressible pump defined within said prosthesis, said pump adapted for fluid communication with said tubular portion, said reservoir and said pump in fluid communication, such that fluid may be transferred from said reservoir to said tubular portion to transform said prosthesis from the flaccid to the erect state.

31. The prosthesis of claim 30 wherein said tubular portion is substantially nondistensible.

32. The prosthesis of claim 31 wherein said tubular sleeve is resilient.

33. The prosthesis of claim 30 wherein said reservoir and said pump are located on opposite sides of said chamber section.

* * * * *